(12) United States Patent
Asfora et al.

(10) Patent No.: US 10,792,053 B2
(45) Date of Patent: Oct. 6, 2020

(54) PRESS SYSTEM FOR SETTING A SURGICAL DEVICE

(71) Applicant: SICAGE LLC, Sioux Falls, SD (US)

(72) Inventors: Wilson Theophilo Asfora, Sioux Falls, SD (US); Daniel S. Savage, Brecksville, OH (US)

(73) Assignee: SICAGE LLC, Sioux Falls, SD (US)

( * ) Notice: Subject to any disclaimer, the term of this patent is extended or adjusted under 35 U.S.C. 154(b) by 237 days.

(21) Appl. No.: 15/799,779

(22) Filed: Oct. 31, 2017

(65) Prior Publication Data
US 2019/0125371 A1    May 2, 2019

(51) Int. Cl.
*A61B 17/17* (2006.01)
*A61B 17/16* (2006.01)
*A61F 2/46* (2006.01)

(52) U.S. Cl.
CPC ...... *A61B 17/1757* (2013.01); *A61B 17/1615* (2013.01); *A61B 17/1655* (2013.01); *A61B 17/1662* (2013.01); *A61B 17/1739* (2013.01); *A61F 2/4603* (2013.01)

(58) Field of Classification Search
CPC . A61B 17/16; A61B 17/1613; A61B 17/1615; A61B 17/1633; A61B 17/1635; A61B 17/1637; A61B 17/1655; A61B 17/1662; A61B 17/1664; A61B 17/1671; A61B 17/17; A61B 17/1739; A61B 17/1757; A61F 2/46; A61F 2/4603; A61F 2/4611
See application file for complete search history.

(56) References Cited

U.S. PATENT DOCUMENTS

| 5,147,367 | A |   | 9/1992 | Ellis |
| 5,676,545 | A |   | 10/1997 | Jones |
| 5,725,581 | A |   | 3/1998 | Branemark |
| 5,735,898 | A |   | 4/1998 | Branemark |
| 6,042,582 | A | * | 3/2000 | Ray ........................ A61F 2/4611 606/86 A |
| 6,048,343 | A | * | 4/2000 | Mathis ............... A61B 17/7098 606/304 |
| 6,063,088 | A | * | 5/2000 | Winslow ............ A61B 17/1757 606/86 A |

(Continued)

*Primary Examiner* — Eric S Gibson
(74) *Attorney, Agent, or Firm* — Fox Rothschild LLP

(57) ABSTRACT

Disclosed herein is a surgical press for setting a surgical device into bone. The surgical press system includes an elongated shaft having a distal portion and a proximal portion. The shaft is configured for insertion into a guide. The surgical press system includes threads extending along an axial portion of the distal end of the shaft. The threads are configured to pull the shaft into bone as the shaft rotates. The surgical press system includes a press element associated with a proximal portion of the shaft such that as the shaft is rotated, the threads pull the shaft into the bone causing the press element to press the surgical device into the bone. The surgical press system includes a collection region located in the distal portion of the shaft and configured to receive bone material removed from the bone due to advancement of the shaft. The surgical press system includes a locating element configured to position the surgical device in a predetermined orientation with respect to the shaft as the press element presses the surgical device into the bone.

22 Claims, 11 Drawing Sheets

(56) References Cited

U.S. PATENT DOCUMENTS

| | | |
|---|---|---|
| 6,135,772 A | 10/2000 | Jones |
| 6,149,686 A | 11/2000 | Kuslich et al. |
| 6,210,376 B1* | 4/2001 | Grayson ............ A61B 17/3472 |
| | | 604/264 |
| 6,287,313 B1* | 9/2001 | Sasso ................. A61B 17/1671 |
| 6,287,343 B1 | 9/2001 | Kuslich et al. |
| 6,391,058 B1 | 5/2002 | Kuslich et al. |
| 6,517,542 B1 | 2/2003 | Papay et al. |
| 6,554,830 B1 | 4/2003 | Chappius |
| 6,565,572 B2 | 5/2003 | Chappius |
| 6,604,945 B1 | 8/2003 | Jones |
| 6,755,835 B2 | 6/2004 | Schultheiss et al. |
| 7,354,442 B2 | 4/2008 | Sasso et al. |
| 7,575,572 B2 | 8/2009 | Sweeney |
| 7,608,062 B2 | 10/2009 | Sweeney |
| 7,717,947 B1 | 5/2010 | Wilberg et al. |
| 7,753,911 B2* | 7/2010 | Ray, III ................ A61F 2/4611 |
| | | 606/86 A |
| 8,062,270 B2 | 11/2011 | Sweeney et al. |
| D667,548 S | 9/2012 | Brannon |
| 8,303,602 B2 | 11/2012 | Biedermann et al. |
| 8,382,808 B2 | 2/2013 | Wilberg et al. |
| 8,574,273 B2 | 11/2013 | Russell et al. |
| 8,808,337 B2 | 8/2014 | Sweeney et al. |
| 8,870,836 B2* | 10/2014 | Sweeney ............ A61B 17/7061 |
| | | 604/264 |
| 8,936,626 B1* | 1/2015 | Tohmeh ............. A61B 17/1615 |
| | | 606/279 |
| 8,956,369 B2 | 2/2015 | Millett et al. |
| 9,131,970 B2* | 9/2015 | Kang ................. A61B 17/7098 |
| 9,173,692 B1 | 11/2015 | Kaloostian |
| 9,198,702 B2 | 12/2015 | Biederman et al. |
| 9,271,742 B2 | 3/2016 | Asfora |
| 9,271,743 B2 | 3/2016 | Asfora |
| 9,295,488 B2 | 3/2016 | Asfora |
| 9,326,779 B2 | 5/2016 | Dorawa et al. |
| 9,326,801 B2 | 5/2016 | Poulos |
| 9,333,018 B2 | 5/2016 | Russell et al. |
| 9,445,852 B2 | 9/2016 | Sweeney |
| 9,526,548 B2 | 12/2016 | Asfora |
| 9,566,100 B2 | 2/2017 | Asfora |
| 9,616,205 B2 | 4/2017 | Nebosky et al. |
| 9,642,656 B2 | 5/2017 | Kotuljac et al. |
| 9,826,993 B2 | 11/2017 | Bake |
| 10,251,688 B2* | 4/2019 | Asfora ................ A61B 17/1615 |
| 2002/0143343 A1* | 10/2002 | Castro ................. A61B 17/1757 |
| | | 606/90 |
| 2003/0196671 A1* | 10/2003 | Sasso ..................... A61B 90/39 |
| | | 128/899 |
| 2004/0092928 A1* | 5/2004 | Sasso ................... A61B 17/863 |
| | | 606/53 |
| 2004/0097932 A1* | 5/2004 | Ray, III ............. A61B 17/1757 |
| | | 606/86 A |
| 2005/0107800 A1* | 5/2005 | Frankel .............. A61B 17/1655 |
| | | 606/92 |
| 2005/0137602 A1* | 6/2005 | Assell ................ A61B 17/7074 |
| | | 606/90 |
| 2005/0273107 A1* | 12/2005 | Stevens .............. A61B 17/1615 |
| | | 606/916 |
| 2006/0116688 A1* | 6/2006 | Boyd .................. A61B 17/1757 |
| | | 606/90 |
| 2007/0106305 A1 | 5/2007 | Kao |
| 2007/0233123 A1 | 10/2007 | Ahmad et al. |
| 2008/0027458 A1 | 1/2008 | Aikins |
| 2008/0077139 A1* | 3/2008 | Landry ............ A61B 17/00234 |
| | | 606/86 A |
| 2009/0142731 A1* | 6/2009 | Kim ........................ A61C 3/02 |
| | | 433/165 |
| 2011/0137352 A1 | 6/2011 | Biedermann et al. |
| 2011/0213426 A1 | 9/2011 | Yedlicka et al. |
| 2012/0010659 A1* | 1/2012 | Angert ............... A61B 17/1757 |
| | | 606/247 |
| 2012/0089195 A1 | 4/2012 | Yedlicka et al. |
| 2013/0065698 A1 | 3/2013 | Biedermann et al. |
| 2013/0245602 A1 | 9/2013 | Sweeney |
| 2013/0267836 A1* | 10/2013 | Mauldin ................... A61B 6/12 |
| | | 600/424 |
| 2014/0012340 A1 | 1/2014 | Beck et al. |
| 2014/0031935 A1* | 1/2014 | Donner ............... A61B 17/1739 |
| | | 623/17.11 |
| 2014/0046381 A1* | 2/2014 | Asfora ................ A61B 17/1615 |
| | | 606/304 |
| 2014/0277165 A1 | 9/2014 | Katzman |
| 2014/0277188 A1 | 9/2014 | Poulos |
| 2015/0100077 A1* | 4/2015 | Geist .................. A61B 17/1757 |
| | | 606/185 |
| 2015/0230844 A1 | 8/2015 | Ellis |
| 2015/0272646 A1* | 10/2015 | Russell .............. A61B 17/7098 |
| | | 606/304 |
| 2015/0313658 A1 | 11/2015 | Kolb |
| 2016/0000489 A1 | 1/2016 | Kaloostian |
| 2016/0008044 A1 | 1/2016 | Sweeney |
| 2016/0143671 A1* | 5/2016 | Jimenez ................ A61B 17/863 |
| | | 606/304 |
| 2016/0143742 A1 | 5/2016 | Asfora |
| 2016/0151100 A1 | 6/2016 | Biedermann et al. |
| 2016/0220291 A1 | 8/2016 | Russell et al. |
| 2016/0310188 A1 | 10/2016 | Marino et al. |
| 2017/0164954 A1* | 6/2017 | Hayes ................ A61B 17/1655 |
| 2018/0360516 A1* | 12/2018 | Frei ...................... A61C 8/0009 |
| 2019/0083271 A1* | 3/2019 | Donner ............... A61F 2/30988 |
| 2019/0125371 A1* | 5/2019 | Asfora ................ A61B 17/1631 |
| 2019/0269469 A1* | 9/2019 | Bush, Jr. ................ A61B 34/20 |
| 2019/0343640 A1* | 11/2019 | Donner ............... A61B 17/1626 |

* cited by examiner

PRESS SYSTEM FOR SETTING A SURGICAL DEVICE

TECHNICAL FIELD

The present invention relates generally to orthopedic surgery. More specifically, techniques, devices, and systems associated with the preparing and setting of surgical devices.

BACKGROUND

Stress across joints and in particular the sacroiliac joint generally is a common cause of pain including lower back pain. Various types of sacroiliac joint stress, including sacroiliac joint disruptions (i.e., separations) and degenerative sacroiliitis (i.e., inflammation) can result from lumbar fusion, trauma, postpartum, heavy lifting, arthritis, or unknown causes. Sacroiliac joint fixation or arthrodesis is sometimes recommended for skeletally mature patients with severe, chronic sacroiliac joint pain or acute trauma in the sacroiliac joint.

Conventional solutions for stabilizing joints and relieving pain in joints typically include the insertion of an implant, such as a metal screw, rod or bar, laterally across the joint. Preparing for the implant has traditionally used a mallet to pound a protective instrument into the region. A more controlled method of pulling protection into the region is desired.

SUMMARY

The summary is illustrative only and is not intended to be in any way limiting. In addition to the illustrative aspects, embodiments, and features described above, further aspects, embodiments, and features will become apparent by reference to the drawings and the following detailed description.

Disclosed herein is a surgical press for setting a surgical device into bone. The surgical the press system includes an elongated shaft having a distal portion and a proximal portion. The shaft is configured for insertion into a guide. The surgical press system includes threads extending along a distal portion the shaft. The threads are configured to pull the shaft into bone as the shaft rotates. The surgical press system includes a press element associated with a proximal portion of the shaft such that, as the shaft is rotated, the threads pull the shaft into the bone causing the press element to press the surgical device into the bone. The surgical press system includes a collection region located in the distal portion of the shaft and configured to receive bone material removed from the bone due to advancement of the shaft. The surgical press system includes a locating element configured to position the surgical device in a predetermined orientation with respect to the shaft as the press element presses the surgical device into the bone.

In accordance with various embodiments, the threads may be configured to tap a thread path into the bone tissue as the threads pull the shaft into the bone. The press may also comprise cutting flutes extending along a distal portion of the cannulated shaft. The threads may be proximal of a proximal termination of the cutting flutes and are suitable to tap a path cut by the cutting flutes. The locating element may include an expanded body portion extending from the shaft proximal of the threads and cutting flutes and distal of the press element. The expanded body portion may be sized to the interior diameter of the surgical device such that the shaft and the surgical device maintains alignment together. The shaft may be cannulated and configured to receive and be guided by a guide pin. The press element is integral to and extends radially from the shaft. The press element may protrudes from the shaft and is larger in diameter than portions of the shaft distal of the press element. The press system may also include the surgical device which includes a sleeve that is suitable to separate the shaft from the surrounding tissue while the cutting flutes cut into the bone and the threads pull the sleeve into the bone.

In accordance with various embodiments, the press element may form a protrusion extending from the shaft that is configured to contact the distal end of the surgical device exerting a force thereon as the threads pull the sleeve into the bone. The protrusion may be annular and configured to contact evenly on the proximal end of the surgical device. The surgical device may be a guide that is configured to establish an angular orientation for the system once the guide is pressed into and set in the bone. The collection region may be configured to accumulate or distribute the bone material to limit interference with the advancement of the shaft in the bone In accordance with various embodiments and disclosed herein is a drill bit. The drill bit may be configured to drill a pilot hole in a bone tissue. The pilot hole may be configured to receive an implant. In accordance with various embodiments, the drill bit comprises an elongated cannulated shaft having a distal end and a proximal end. The drill bit also may comprise cutting flutes extending along a distal portion of the cannulated shaft. The cutting flutes may be configured to form the pilot hole in the bone tissue that receives an implant. The drill bit also may comprise threads extending along a distal portion of the cannulated shaft and proximal of the cutting flutes. The threads may be configured to tap the pilot hole and pull the cannulated shaft into bone tissue as the cannulated shaft rotates.

In accordance with various embodiments, the drill bit may also comprise a press element associated with a proximal portion of the shaft such that as the shaft is rotated the threads pull the shaft into the bone tissue causing the press element to press a surgical device into the bone. The press element may have a larger diameter than the surgical device such that the press element prevents the shaft from advancing farther into the surgical device after initial press between a proximal end of the surgical device and the press element. The protrusion may be annular and configured to contact evenly on the proximal end of the surgical device. The drill bit may also comprise a locating element configured to position the surgical device in a predetermined orientation with respect to the shaft as the press element presses the surgical device into the bone. The cannula may be sized to slide over a guide pin. The shaft may include a shank on the proximal end suitable to engage a handle or drill. The drill bit may also comprise a collection region located distal of the threads, the collection region forming a volume that is configured to accumulate or distribute material removed by the threads.

In accordance with various embodiments, a method for setting a surgical instrument into a bone tissue is provided for. The method may comprise aligning a drill bit over a guide pin. The drill bit may be inserted through the surgical instrument. A pilot hole may be drilled in the bone tissue with cutting flutes that extend along a distal portion of the drill bit. Threads may be cut into the pilot hole with threads located on the drill bit proximal of the cutting flutes. The drill bit may be pulled into the pilot hole with the engagement between the threads and the bone tissue. The surgical instrument may be pressed into the cortex of the bone tissue with a pressing element located on the drill bit proximal of the threads. The drill bit may be pulled from the pilot hole and out of the surgical instrument leaving the surgical instrument imbedded into the bone tissue. An implant may be threaded into the pilot hole.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several examples in accordance with the disclosure and are therefore not to be considered limiting of its scope, the disclosure will be described with additional specificity and detail through the use of the accompanying drawings, in which:

DETAILED DESCRIPTION

Figure 1A:
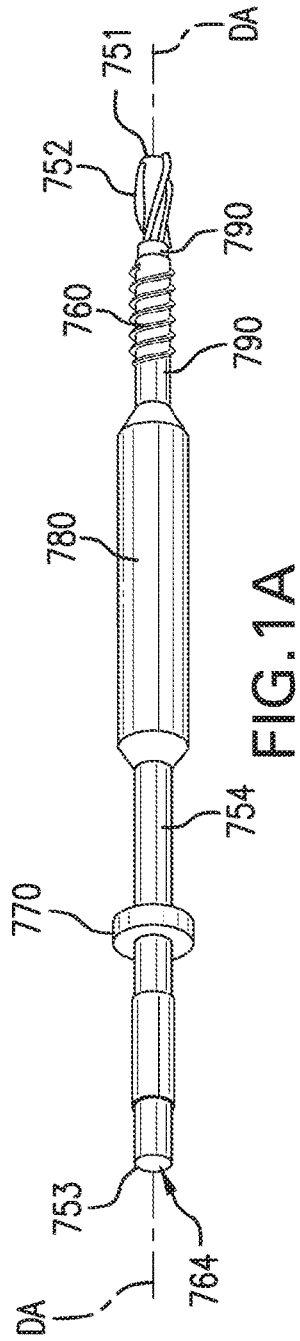
FIG. 1A is a perspective view of a press system for setting a surgical device into bone according to one embodiment.

In the following detailed description, reference is made to the accompanying drawings, which form a part hereof. In the drawings, similar symbols typically identify similar components, unless context dictates otherwise. The illustrative examples described in the detailed description, drawings, and claims are not meant to be limiting. Other examples may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are implicitly contemplated herein.

Techniques for joint fusion are described, including systems, apparatuses and processes for fusing a joint. Systems and apparatuses for fusing a joint include a cage (i.e., a cannulated cage), a surgical device (e.g. a drill guide/tissue protector assembly), a guide, a depth gauge, a cannulated drill bit (e.g., an adjustable cannulated drill bit that employs a stop collar), a driver, a parallel guide, and a plunger distance tool. As used herein, the term "cannulated" refers to having a cannula, or a hollow shaft. In some examples, the cage may be inserted or implanted into tissue (e.g., bone, cartilage, or other tissue in the joint). As used herein, the term "implant" or "implantation" refers to inserting or insertion into a part of a body. For example, a bone cage may be implanted into a joint (e.g., a sacroiliac joint). In some examples, the cage may have a cannula and radial fenestrations in which therapeutic materials may be packed. Such therapeutic materials may include osteogenic compounds (e.g., bone morphogenetic protein, or other osteogenic compounds that may ossify tissue in the joint), osteoconductive materials (e.g., demineralized bone, hydroxyapatite, or other material that promotes bone growth), antibiotics, steroids, contrast materials, or other materials that may beneficial to fusing the joint, treating inflammation or other conditions in the joint, or enabling the visualization of the area within and adjacent to an implanted bone cage. In some examples, the bone cage may be a screw or screw type device having threads. In some examples, the screw may have one or more rows or groups of helical fenestrations along the wall (i.e., the shaft of the cage defining the cannula) of its shaft to allow the material packed inside the cannula of the cage to contact (e.g., touch, seep into, affect, communicate with, or otherwise physically contact) tissue adjacent to, surrounding, or even within, the cage. In some examples, various tools may be used to insert a cage into a location on a joint, and to prepare the location for the insertion procedure. Such tools may include an implantation assembly, which may comprise a surgical device (e.g. tissue protector); a guide; a depth gauge; a cannulated drill bit; a driver; a parallel guide; a packing plunger, which may comprise a packing tube, a plunger and a loading port; a plunger distance tool; and other tools.

In some examples, a guide may be inserted first into a joint at a desired location, in a lateral position across the joint. In some examples, a surgical device (e.g. tissue protector) assembly may be used, along with the guide, to guide the preparation (i.e., drilling) of a pilot hole as well as to guide insertion of a cannulated cage or other implant while forming a barrier between the preparation site and the surrounding tissue. In some examples, a cannulated drill bit may be used with the surgical device (e.g. tissue protector and/or drill guide) to drill the pilot hole. In some examples, a driver or screw driver may be used to insert the cage into the pilot hole. The terms "driver" is used herein to refer to a tool with a tip configured to engage the head of a screw or similar device, the tool being useful for rotating a screw or otherwise manipulating the screw to drive the screw or, in this case, cage into place in a joint. In some examples, a parallel spacer device may be used to space another guide in preparation for insertion of another cage. In some examples, a packing plunger assembly may be used to pack the cage with the above-mentioned materials. The packing plunger may be used to pack materials into the cage either or both pre- and post-insertion of the cage into the joint, and may be used with or without the surgical device (e.g. tissue protector) assembly.

Figure 1B:
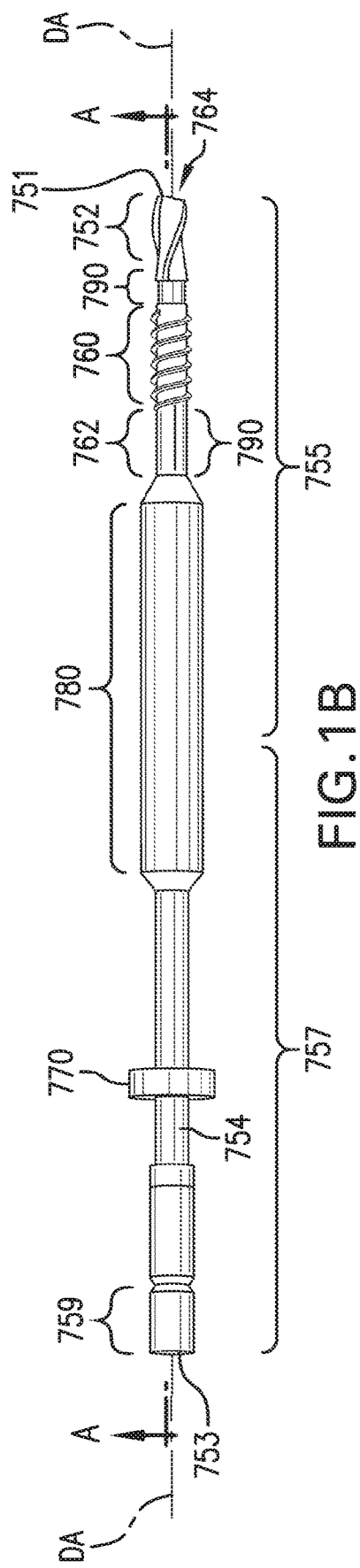
FIG. 1B is a side view thereof.
Figure 1C:
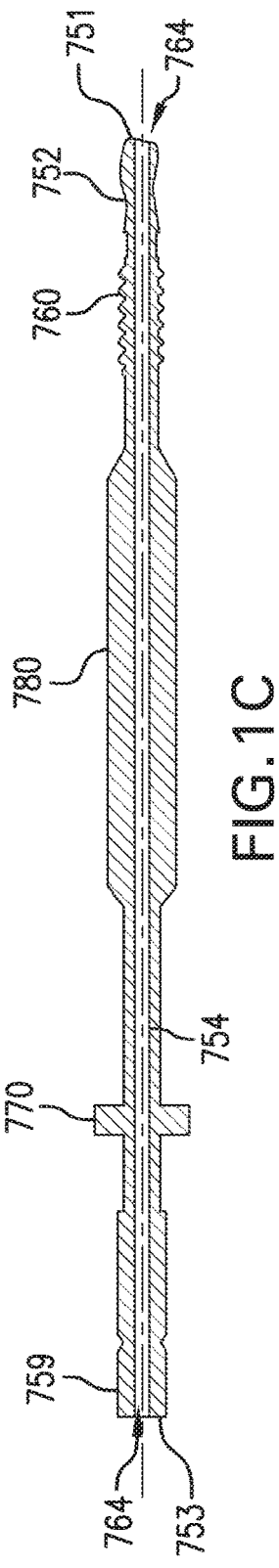
FIG. 1C is a cross section view thereof taken along cross section line A-A of FIG. 1A.

FIG. 1A is a perspective view of a surgical press system 750 for setting a surgical device into the bone according to one embodiment; FIG. 1B is a side view thereof; and FIG. 1C is a cross section view thereof taken along cross section line A-A of FIG. 1A. In accordance with various embodiments, the surgical press system 750 is configured to force the surgical device into the bone. In accordance with one embodiment, the surgical press system 750 is configured to pull the surgical device into the bone by threading into the bone itself. In one example, the surgical press is an elongated screw that pulls the surgical device into the bone while also orienting the surgical device relative to the surgical press or to a guide (e.g. pin, wire, or similar surgical guide). In another example, the surgical press is a drill bit that bores into the bone and also pulls the surgical device into the bone while orienting the surgical device. In accordance with various embodiments, the surgical press system 750 includes an elongated shaft 754 having a distal end 751 and a proximal end 753 with an axis DA. The shaft may include one or more of a cannulation 764, a locating element 780, pulling threads 760, a press element 770, cutting flutes 752, and/or a collection region 790. The surgical press system 750 can include any combination of these structures that is suitable to achieve the various functionalities of the surgical press system 750 discussed herein. In accordance with various embodiments, the shaft 754 of the surgical press system 750 is inserted into a surgical instrument (e.g. drill guide, tissue protector or the like). The shaft 754 passes through the surgical instrument (e.g. drill guide, tissue protector or the like) such that the proximal end 753 engages the bone tissue or a bore within the bone tissue. In one example, the surgical press system 750 is a threaded drill bit suitable to pull the surgical device into the bone tissue. In various embodiments, the surgical press system 750 is cannulated such that it can receive a guide wire and be directed to the bone tissue through the surgical instrument.

In accordance with various embodiments, the surgical device can be any suitable surgical instrument that is secured against or set into the bone or in a particular example set into the cortex of the bone (e.g. Ilium I). In various embodiments, the surgical instrument is a surgical guide such as a drill guide, screw guide, dilator guide, or an embedded surgical device (e.g. tissue protector) or similar suitable device. As discussed herein with reference to FIGS. 1A-E, the surgical instrument is shown as and described as the drill guide 450 as an example in order to clearly convey the various features in an efficient manner. It will be understood to a person of ordinary skill in the art, however, that the various concepts discussed under the example of the drill guide 450 is or can be extended to other surgical instruments according to the knowledge and understanding of a person of ordinary skill in the art In accordance with various embodiments, the shaft 754 is formed from a suitable material that provides sufficient strength to rotate the shaft 745 within the surgical device and/or within the cortex of the bone. The outside diameter of the shaft 754 is configured to fit within the surgical instrument which will be referred to via the example of the drill guide 450. In some examples, the outside diameter may be significantly smaller than the drill guide 450, such that the drill guide 450 does not provide significant support to the surgical press system 750 or function as the primary locating tool for the surgical press system 750.

In accordance with one embodiment, the shaft 754 may include the locating element 780. The locating element 780 may have a larger diameter than the threads and configured to engage and form a close tolerance fit within the surgical device to position the drill guide 450 in a predetermined orientation with respect to the shaft as the press element pushes the drill guide 450. Accordingly, the drill guide 450 (or other suitable surgical devices) may function to guide the surgical press system 750 providing significant support and locating functionality to the surgical press system 750 by having an inner diameter that is substantially the same size as the outer diameter of the surgical press system 750. The variance in sizes being sufficient to allow the surgical press system 750 to slide and rotate within the surgical device (e.g. tissue protector). In accordance with various embodiments, the locating element 780 is an expanded body portion formed of an annular protrusion extending outwardly from the shaft. The expanded body portion is sized to the interior diameter of the guide such that the shaft 754 maintains alignment of the surgical instrument (e.g. drill guide 450) relative to a guide (e.g. guide pin 418) or the surgical instrument (e.g. drill guide 450) maintains alignment of the shaft 754 relative to an orientation of the surgical instrument (e.g. drill guide 450).

In accordance with one embodiment, the shaft 754 may include threads 760. The threads 760 extend axially along a portion of the distal end 755 of the shaft 754. The threads 760 are configured to engage with the bone tissue sufficiently to apply a longitudinal force along the shaft in a way that pulls the shaft 754 into bone along with the surgical instrument (e.g. drill guide 450) as the shaft 754 rotates. In some embodiments, the threads may be tapping threads that are configured to tap a threaded path into the bone tissue, specifically the cortex of the bone as the threads rotate. In accordance with various embodiments, the major diameter of the threads may be slightly less than the minor diameter of the implant. This relationship would allow the implant to fully fill the space cut by the threads. In various examples, the length of threads is approximately 3 mm-10 mm. It may be appreciated that any length suitable to allow the screw to fully or partially penetrate the cortex can used. In some embodiments, the thread profile would be a buttress format similar to bone screw threads, as it has been shown to provide an effective means of achieving load transfer. The depth of threads depends on the application. For example, in a large diameter implant, thread depths can be greater than 2 mm. In smaller applications, this thread depth can be from ½ mm to 2 mm.

In accordance with one embodiment, the shaft 754 may include the press element 770. The press element 770 is associated with the portion of the shaft that is positioned to engage the surgical instrument (e.g. drill press 450) when the surgical instrument is positioned to be forced into the bone. In one embodiment, the press element 770 is associated with a proximal portion 753 of the shaft 754 and configured to engage a proximal end 451 of a surgical device such that as the shaft is rotated the threads pull the shaft into the bone causing the press element to press the surgical device into the bone.

In accordance with various embodiments, the distal portions of the shaft are structured such that they can be received into the surgical instrument (e.g. drill press 450). The distal portions of the shaft are structured such that they limit advancement into the surgical instrument (e.g. drill press 450). For example, the press element 770 may limit the forward advancement of the distal portions of the shaft into the surgical instrument (e.g. drill press 450). In a particular example, the press element 770 may have a larger diameter than the threads 760, the locating element 780, and/or any other feature distal of the press element 770. In particular, the press element 770 may have a larger diameter (or size in any radial direction from axis DA if the press element is not round) than the surgical instrument (e.g. drill press 450). The size of the press element 770 may be sufficiently large so that the distal portions of the surgical press system 750 are received into the surgical instrument (e.g. drill press 450) but the press element 770 stops the surgical press system 750 from advancing further into the surgical instrument (e.g. drill press 450). Despite the fact that the press element 770 stops the surgical press system 750 from advancing further into the surgical instrument (e.g. drill press 450), the continued rotation of the surgical press system 750 can cause continued advancement of the threads 760 into the bone resulting in the surgical press system 750 continuing to advance into the bone. Since the press element 770 stops the surgical press system 750 from advancing further into the surgical instrument (e.g. drill press 450), the press element 770 instead causes the surgical instrument (e.g. drill press 450) to advance into the bone.

In accordance with one embodiment, the press element 770 may be an integral part of the shaft 754. Accordingly the press element 770 is fixed relative to the rest of the shaft. In other embodiments, the press element 770 is adjustable relative to the rest of the shaft 754. The adjustability may allow the surgical press system 750 to accommodate different sizes or configurations of surgical instruments.

In accordance with one embodiment, the shaft 754 may include a cutting tip 752. In such embodiments, the cutting tip 752 is formed by one or more flutes extending along the distal axial portion 755 of the shaft 780. The flutes extend from the distal end 751 towards the proximal end 753. The threads 760 are proximal of a proximal termination of the cutting flutes 752. The cutting flutes 752 may bore through the cortex of the bone and into the bone prior to the threads 760 engaging the bone and pulling the surgical press system 750 into the bone.

In accordance with various embodiments, the shaft 754 may include the collection region 790. The collection region is a portion of the shaft 754 that provides a region or volume to collect debris (e.g. bone debris) that accumulates in the path of the surgical press system 750 as the surgical press system 750 advances into the bone. In some examples, the debris may be formed by the threads tapping into the bone. In other examples, the debris may be formed by cutting flutes on the surgical press system 750 drilling into the bone. In accordance with various embodiments, the collection region 790 is located distally and/or proximally of the threads 760 and configured to receive bone material produced by a cutting tip on the surgical press system 750 and/or the threads 760 themselves.

In accordance with various embodiments, the locating element 780 includes an expanded body portion extending from the shaft. The locating element 780 may be located centrally on the shaft 754, allowing it to engage within the surgical instrument (e.g. drill guide) but not interfere with the threads 760 or cutting flutes 752 as variously included depending on the embodiment. For example, the locating element 780 may be located proximally of the threads 760 and/or cutting flutes 752. For example, the locating element 780 may be located distally of the press element 770.

In accordance with one embodiment, the shaft 754 is cannulated having the cannula 764 extending along the axis DA. In some examples, cannula 764 is sized to fit over a guide (e.g., guide 418). The surgical press system 750 may be slid down over the guide wire 418 thereby accurately locating the surgical press system 750 based on the insertion location of the guide wire 418 into the bone.

A driver handle 956 (shown in FIGS. 1D and 1E) may receive the shank 709 allowing a user to apply a torque to the surgical press system 750. The torque applied to the surgical press system 750 can result in both the drilling of the bone via the cutting tip 752 and the advancing of the surgical press system 750 into the bone via the threads 760. Once contact is made with the surgical instrument 450, the surgical instrument 450 is also advanced into the bone due to the torque applied by the handle 956.

As discussed above, the surgical instrument 450 may include a variety of devices. In one embodiment, the surgical instrument 450 is a bone guide having a sleeve 454 thereof protecting the tissue surrounding the site in which the cutting tip 752 is advancing into the bone. The sleeve 454 protects the surrounding tissue from being damaged by the cutting action. The surgical press system 750 may then form a hole through one or more bones (e.g., Ilium I and/or Sacrum S). As a drill guide, the surgical instrument 450 may also provide support to the drill, or subsequently place an implant once the drill guide is set into the bone by the surgical press system 750. This support allows the drill guide to set an angular orientation for the system once the guide is pressed into and set in the bone.

Figure 1D:
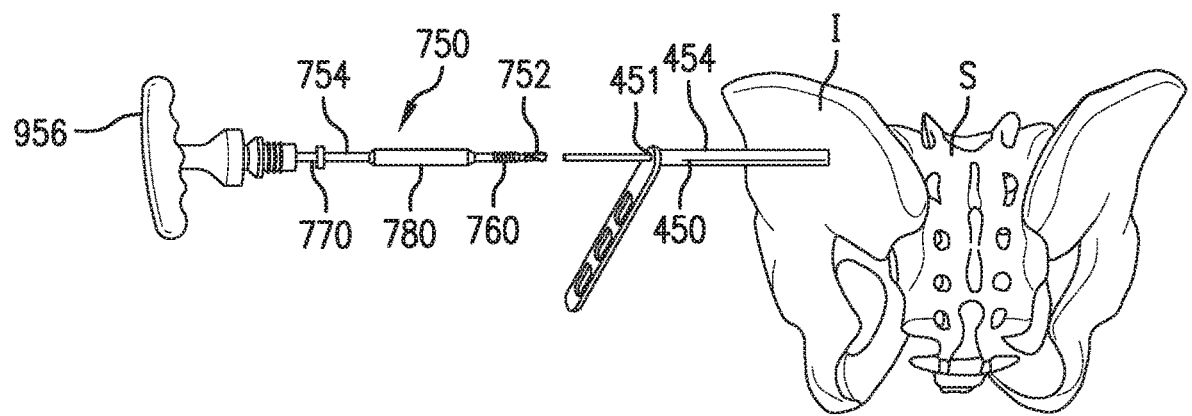
FIG. 1D is a perspective view of the press system of FIG. 1A inserting a surgical device into bone.
Figure 1E:
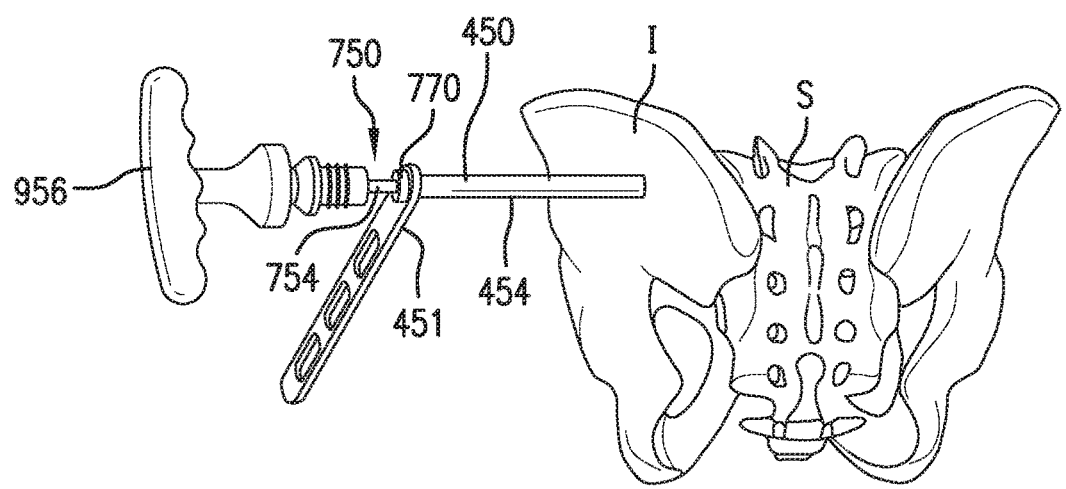
FIG. 1E is a perspective view of the press system of FIG. 1A setting a surgical device into bone.

FIG. 1D is a perspective view of the surgical press system 750 preparing the bone for insertion of an implant (e.g. bone cage discussed below) for joint fusion according to one embodiment; and FIG. 1E a perspective view of the surgical press system 750 engaged with the surgical instrument 450 (e.g. the drill guide illustrated) and setting the instrument into the bone (e.g. the Ilium I) for subsequent insertion of an implant (e.g. bone cage discussed below) for joint fusion according to one embodiment. In accordance with various embodiments, the surgical press system 750 is aligned along the guide pin 418 and through the surgical instrument 450. In some embodiments, the surgical press system 750 bores into and/or threads into the bone functioning as a drill bit. In some embodiments, the press presses the surgical instrument 450 (e.g. drill guide) into the bone tissue. The surgical press system 750 is removed from the guide pin.

Figure 2A:
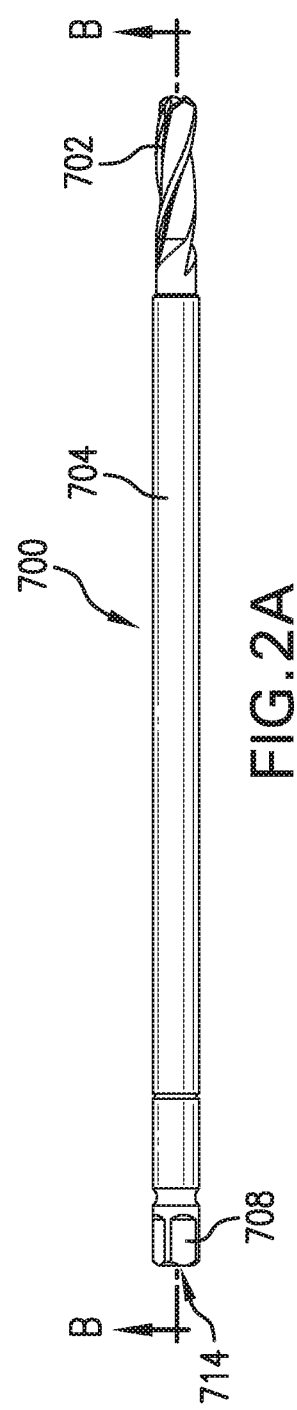
FIG. 2A is a side view of a drill for setting a surgical device into bone according to one embodiment.
Figure 2B:
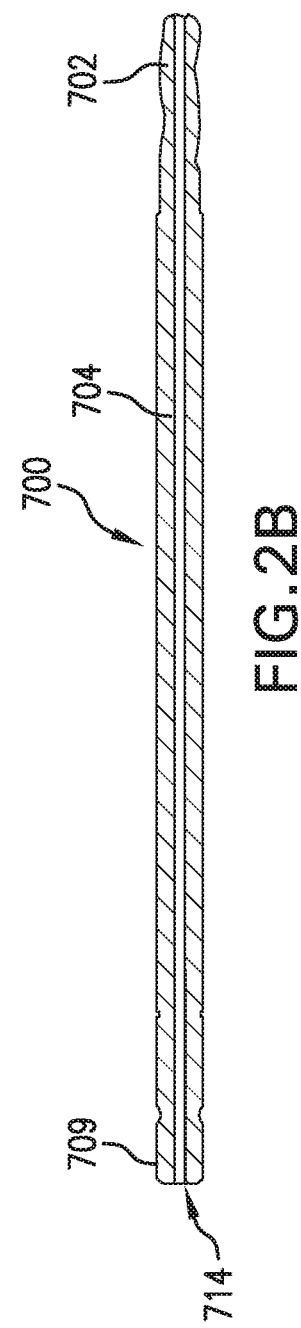
FIG. 2B is a cross section view thereof taken along cross section line B-B of FIG. 2A.

FIGS. 2A and 2B illustrate a side view of an exemplary cannulated drill bit and of drilling a pilot hole for insertion of a cage for joint fusion. Here, the cannulated drill bit 700 may include the cutting tip 702, the body 704, and the shank 709. As used herein, "drill bit" refers to any cutting tool configured to create substantially cylindrical holes, and "shank" refers to an end of the drill bit, usually the end opposite of the cutting tip, configured to be grasped by a chuck of a drill, handle or other torque applying device. In some examples, the cannulated drill bit 700 may be configured to drill a pilot hole to a predetermined depth. For example, the cutting tip 702 may be configured to cut cylindrical holes into the bone and/or joint when torque and axial force is applied to rotate the cutting tip 702 (i.e., by a drill). In some examples, the cannulated drill bit 700 may be adjustable, and thereby configured to drill a range of depths using depth markings. The outside diameter of the cannulated drill bit 700 may be configured to fit within a surgical device (e.g., tissue protector 400). In some examples, the outside diameter may be significantly smaller than the surgical device (e.g. tissue protector 400), such that the surgical device (e.g. tissue protector) does not provide significant support to the drill bit 700 or function as the primary locating tool for the drill bit 700. In other examples, the tissue protector 400 may function as the drill guide, providing significant support and locating functionality to the drill bit 700 by having an inner diameter that is substantially the same size as the outer diameter of the drill bit 700. The variance in sizes being sufficient to allow the drill bit 700 to slide and rotate within the tissue protector.

In some examples, a desired drilling depth (i.e., depth of a pilot hole) may be the same or similar to the depth of a guide that has been inserted into the bone and/or joint. In other examples, the desired drilling depth may be offset (i.e., less deep) by a predetermined amount (e.g., a few millimeters or other offset amount). For example, if a guide has been inserted 40 mm deep into the sacroiliac joint, a corresponding desired drilling depth for the pilot hole may be 40 mm, or it may be 40 mm minus the predetermined offset that may be selected (i.e., if the predetermined offset is 3 mm, then the desired drilling depth in this example would be 37 mm).

The cannulated drill bit 700 includes the cannula 714. In some examples, the cannula 714 are sized to fit over a guide (e.g., guide 418). A driver handle 906 may receive the shank 709 allowing a user to apply a torque to the drill bit 700. The drill bit 700 may be slid down over the guide wire 418 thereby accurately locating the drill bit 700 based on the insertion location of the guide wire 418 into the bone. Tissue protector 400, particularly the sleeve 404, thereof protects the soft tissue surrounding the drill site from being damaged by the drilling action. In various examples the soft tissue includes muscle tissue, tendons, ligaments, nerve tissue, blood vessels and the like. Other surgical devices discussed herein performs similar functions to the tissue protector 400 (e.g. the surgical device 450 performs similar functionality). The drill may than form hole through one or more bones (e.g., Ilium I and/or Sacrum S).

Figure 2C:
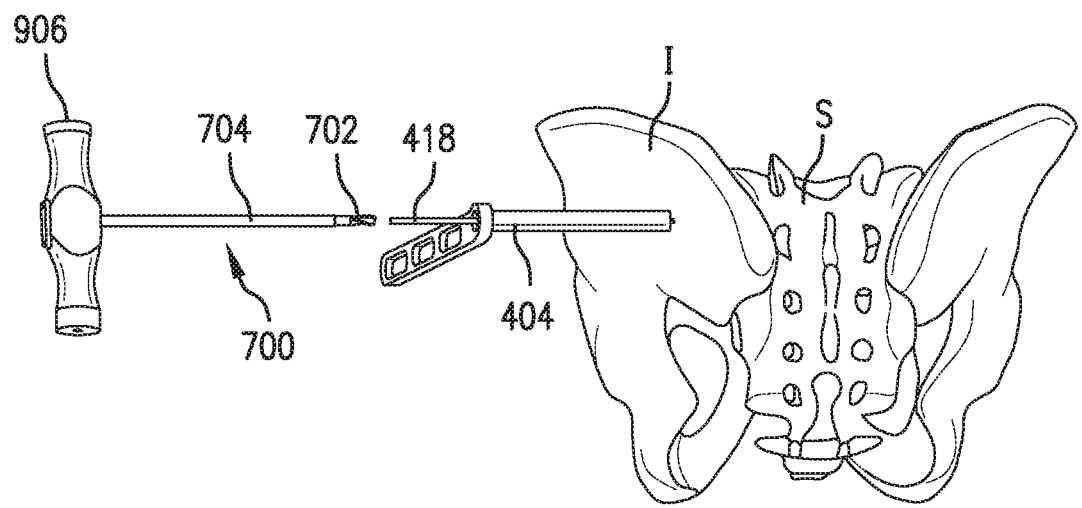
FIG. 2C is a perspective view of the drill of FIG. 2A inserting into a tissue protector.
Figure 2D:
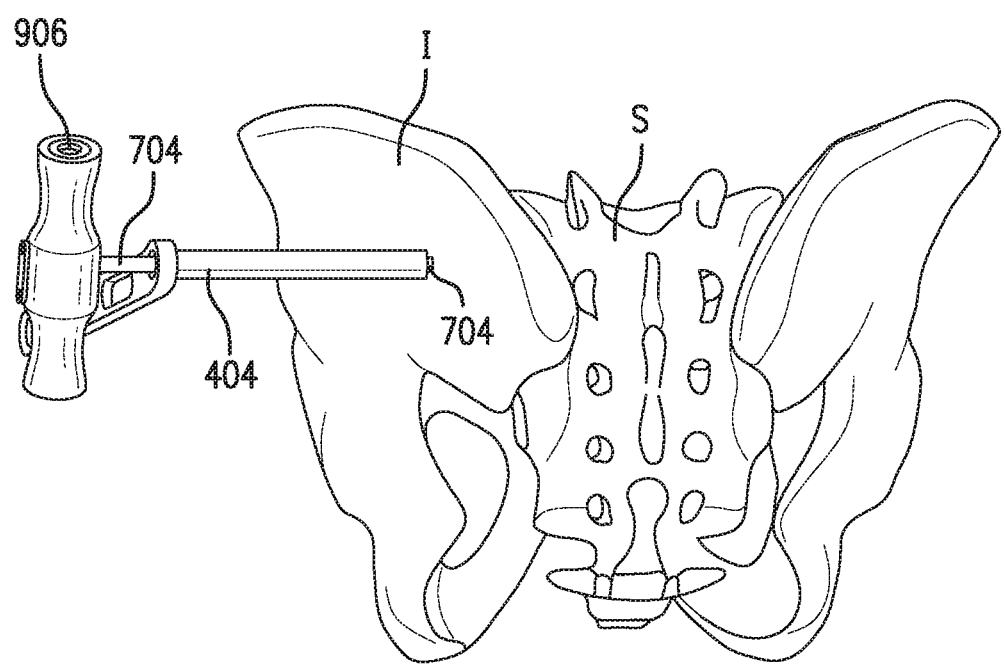
FIG. 2D is a perspective view of the drill of FIG. 2A drilling into a bone.

FIG. 2C is a perspective view of the surgical press system 700 preparing the bone for insertion of an implant (e.g. bone cage discussed below) for joint fusion according to one embodiment and FIG. 2D a perspective view of the surgical press system 700 engaged with the surgical instrument 400 (e.g. the drill guide illustrated) and setting the instrument into the bone (e.g. the Ilium I) for subsequent insertion of an implant (e.g. bone cage discussed below) for joint fusion according to one embodiment. In accordance with various embodiments, the surgical drill bit 700 is aligned along the guide pin 418 and through the surgical instrument 400. In some embodiments, the surgical press system 700 bores into and/or threads into the bone functioning as a drill bit. In some embodiments, the drill bit 700 bores into the bone and the tissue protector floats outside of the bone protecting the surrounding tissue from the drill and implants. In such an embodiment, the guide pin 418 controls and orients the system. The drill bit is removed from the guide pin preparing the sight for an implant.

Figure 3:
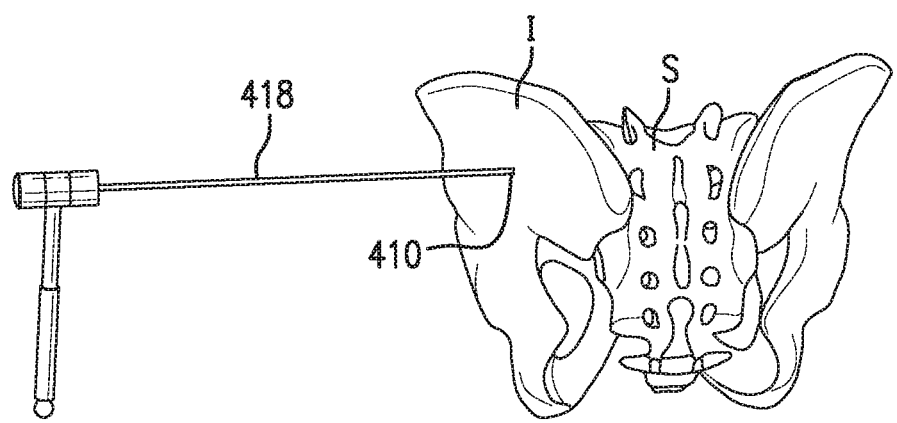
FIG. 3 illustrates a guide pin being set in a sacroiliac joint according to one embodiment of a surgical procedure for joint fusion.

FIG. 3 illustrates an exemplary guide pin 418. In some examples, guide pin 418 may be a medical grade sterile metal guide such as a wire or pin (e.g., Kirschner wire, Steinmann pin, or other metal pin) suitable for use in medical procedures. In some examples, the guide may be another type of medical device suitable to form a primary orientation during surgery. Such alternative guides can include drill guides or tissue protectors. In some examples, guide pin 418 may be used for alignment and guidance of a tissue protector (e.g., tissue protector 404), an implant (e.g., a cage or other implant), and other tools into the Ilium I, the Sacrum S, or the joint there between. The guide pin 418 can be set into the patient via twisting, hammering, pressure or any other suitable method. In a particular example, mallet 417 drives the guide pin 418 into the Ilium and/or the Sacrum. In some examples, guide tip 410 may form a trocar for introducing tissue protector assembly 400 into the bone.

Figure 4A:
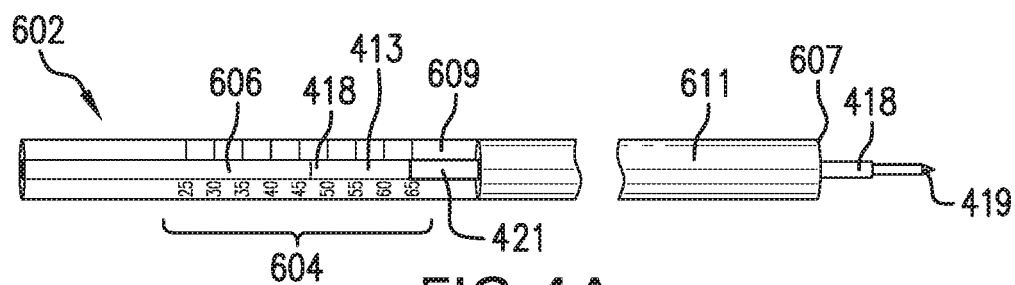
FIG. 4A illustrates a depth gauge according to one embodiment for determining the depth of a pilot hole to be drilled for insertion of a cage for joint fusion.
Figure 4B:
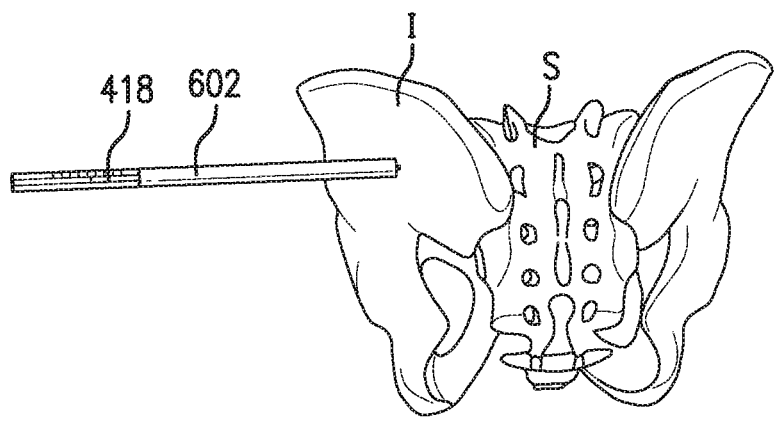
FIG. 4B is a view thereof installed over a guide being set in a sacroiliac joint in the procedure of FIG. 3.

In accordance with various embodiments, the guide pin 418 may be insulated along its mid portion as shown by insulation 421 in FIG. 4A. The two ends 413 and 419 may be exposed conductive material (e.g. metal) allowing an electrical current to be inputted at one end 413 and delivered at the other end 419. This allows a user to electrically stimulate the pin which will elicit contraction of the respective muscle if it is near a nerve root. Electromyography is also monitored to pick up muscle contraction. In one example, this embodiment of the guide pin 418 is a centrally insulated Steinman pin.

FIG. 4A illustrates an embodiment of a depth gauge 602 for determining the depth of a guide to be inserted into the Ilium I and/or Sacrum S. In various embodiments, depth gauge 602 includes depth markings 604, channel 606, and distal contact surface 607. In various examples, the channel 606 is formed along an exposed wall 609 of the depth gage. The channel 606 transitions into an enclosed channel through a lower body portion 611. The contact surface 607 is located on the distal end of the lower body portion 611 and is suitable to contact the Ilium I. The guide pin 418 may then be slid into the depth gauge 602 to the desired depth as measured on the depth markings 604. In some examples, depth gauge 602 may be configured to determine the depth in which guide pin 418 is inserted into the bone and/or joint. In some examples, depth gauge 602 may include depth markings 604, which can measure the depth in which the guide pin 418 is driven into the Ilium. In some examples, the depth markings 604 may indicate a range of 25-65 mm depths. In other examples, the depth gauge 602 may have different depth markings, and thus indicate a different range of depths. The number in depth markings 604 that corresponds to the location of the end of guide 418 may indicate the depth of guide pin 418. In other examples, the depth markings 604 can indicate a different depth that may correspond and be calibrated to the depth of guide pin 418 (e.g., depth markings 604 may indicate a desired drilling depth for a pilot hole, a depth of a cage to be implanted, or other depth that is associated with the depth of guide pin 418, and may thus be measured against the depth of guide pin 418). In other examples, the depth gauge 602 may include more or fewer elements and is not limited to the examples described.

Figure 5A:
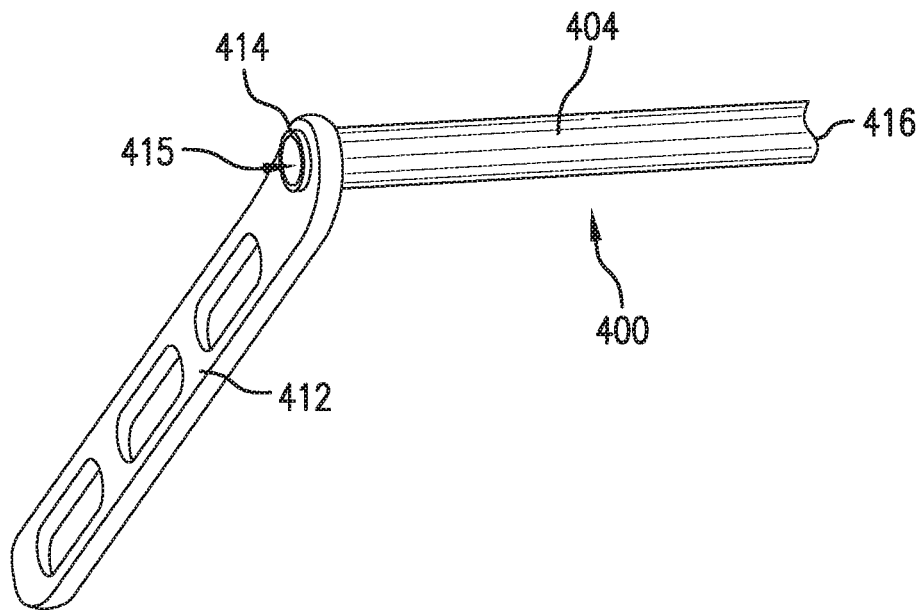
FIG. 5A illustrates a tissue protector according to one embodiment.
Figure 5B:
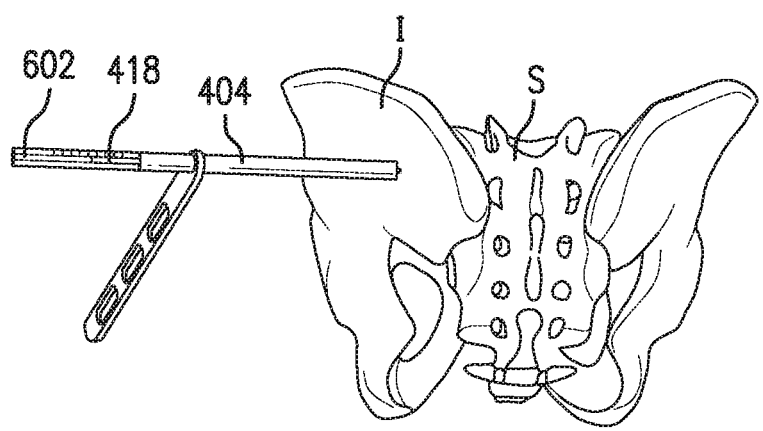
FIG. 5B is a view thereof placed over a guide and set in a sacroiliac joint in the procedure of FIG. 3.

FIGS. 5A and 5B illustrate a tissue protector assembly 400. The tissue protector assembly may include sleeve 404 and handle 412. In some examples, tissue protector sleeve 404 may include a tissue protector head 414, and tissue protector tip 416. In some examples, sleeve 404 has a hollow shaft 415 having a close fit to one or more of the depth gauge 602, the cage 100, and or a drill 700. In some embodiments, the guide 481 may be utilized with a guide sleeve. The guide sleeve can receive into the guide sleeve. The guide sleeve can then be inserted into the tissue protector. In various embodiments, the guide sleeve includes a close tolerance to the interior of the channel 415 of the tissue protector so that the guide is accurately positioned in the tissue protector 404. In some embodiments, the guide 418 is centered in the tissue protector 400. In other embodiments, the depth gauge 602 functions as the guide sleeve. In some examples, the outer diameter of sleeve (e.g., depth gauge 602) shaft is shaped to fit inside the cannula of tissue protector 400, which has an internal diameter that may be configured to accommodate tools and implants (e.g., cages 100, and the like) having a larger diameter than a guide. For example, the diameter of tissue protector 404's cannula 415 may correspond to (i.e., be sized to fit) the head or outer diameter on an implant (e.g., cages 100). In some examples, the internal surface of tissue protector 400 may be configured to guide an implant (e.g., cage 100) inserted into tissue protector 400 from tissue protector head 414 and through to tissue protector tip 416.

In some examples, tissue protector tip 416 may have spikes, teeth, wedges, or other structures, to engage a bone. As shown, tissue protector tip 416 is engaged with an ilium (i.e., its spikes, teeth, wedges or other structure for engaging a bone, are embedded in the ilium). In some embodiments, the tissue protector tip 416 does not embed into the bone but merely increases friction such that the tissue protector tip 416 does not slip on the exterior of the bone. In other examples, tissue protector assembly 400 may be formed differently and is not limited to the examples described.

FIG. 5B illustrates an exemplary tissue protector assembly placed over a guide. Here, diagram 420 may include tissue protector sleeve 404, handle 412, tissue protector head 414, tissue protector tip 416 and guide 418 and depth gage 602 (functioning as a guide sleeve for a pin or wire). Like-numbered and named elements in this view may describe the same or substantially similar elements as in previous views (e.g., FIG. 4A).

Figure 6A:
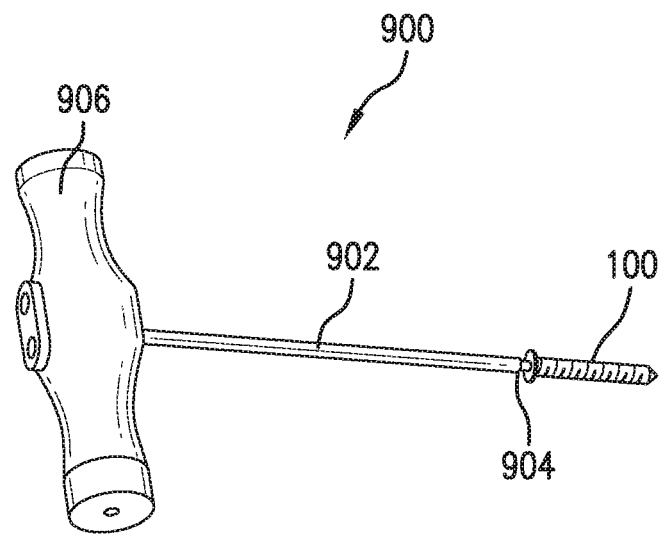
FIG. 6A is a perspective view of a driver for driving a bone cage for insertion of the cage for joint fusion according to one embodiment.
Figure 6C:
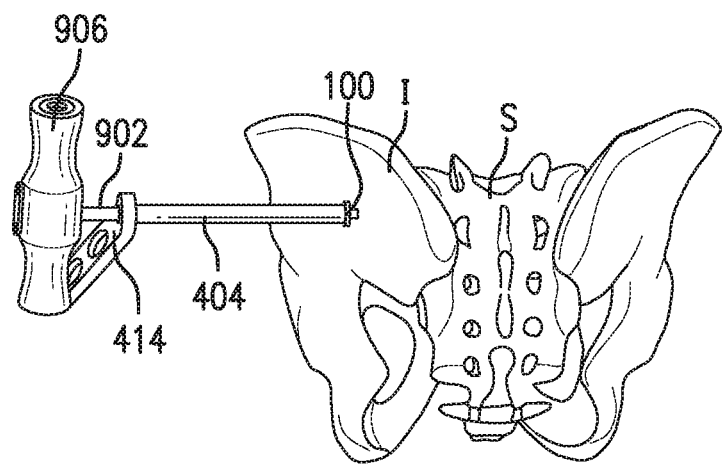
FIG. 6C is a side view of the driver of FIG. 6A driving a bone cage into a joint for fusion in the procedure of FIG. 3.
Figure 6B:
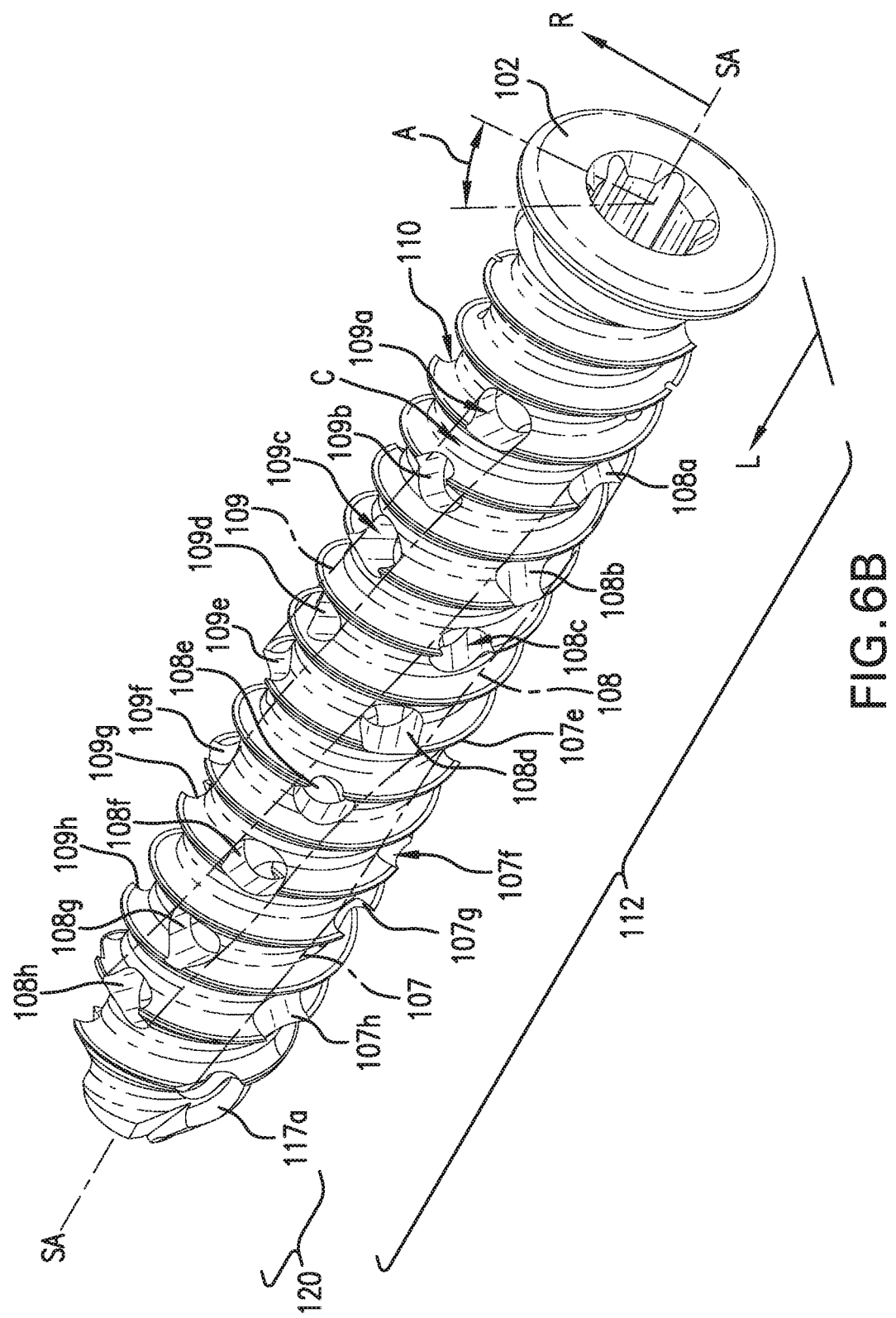
FIG. 6B is a perspective view of a bone cage shown in FIG. 6A.

FIGS. 6A and 6C illustrate an exemplary driver 902 for inserting an implant into the joint for fusion. As used herein a cage 100 is provided as an example but it is noted that bone screws for joint fusion can also be used in accordance with the various embodiments discussed herein. Various examples of the bone cage 100 are further disclosed in co-pending application entitled "Bone Cage With Helically Arranged Fenestrations" having application Ser. No. 15/798,984 filed herewith on the same date, which is incorporated herein by reference in its entirety. For reference purposes, FIG. 6B illustrate a perspective view of an exemplary bone cage 100. In accordance with various embodiments, the cage 100 includes head 102, tip 104, one or more groups of helical fenestrations (e.g., fenestration groups 107-110), threads 112, and tapered end 120. In some examples, cage 100 may be fabricated, manufactured, or otherwise formed, using various types of medical grade material, including stainless steel, plastic, composite materials, or alloys (e.g., Ti-6Al-4V ELI, another medical grade titanium alloy, or other medical grade alloy) that may be corrosion resistant and biocompatible (i.e., not having a toxic or injurious effect on tissue into which it is implanted). In some examples, threads 112 may be a helical ridge wrapped around an outer surface of cage 100's shaft. In some examples, cage 100 may be cannulated having a cannulated opening 124 formed by a hollow shaft that extends from head 102 to tip 104. Cage 100 may vary in length (e.g., ranging from approximately 25 mm to 50 mm, or longer or shorter) to accommodate size and geometric variance in a joint. Other dimensions of cage 100, including major 132 and minor 133 diameters of threads 112, also may vary to accommodate size and geometric variance in a joint. In some examples, an outer surface of cage 100's shaft may taper from head 102 to tapered end 120, and thus threads 112 also may taper (i.e., be a tapered thread) from head 102 to tapered end 120 (e.g., having a range of major and minor diameters from head 102 to tapered end 120). In some examples, the tapering of threads 112, as well as tapered end 120, aids in guiding the cage through a pilot hole. In other examples, head 102 and threads 112 may be sized to fit within a tool or instrument, for example, a tissue protector 400, as described herein.

In some examples, cage 100's hollow shaft, or cannula, may be accessed (i.e., for packing material into) through an opening 124 in head 102. In some examples, head 102 may have a flat or partially flat surface (e.g., pan-shaped with rounded edge, unevenly flat, or other partly flat surface). In other examples, head 102 may have a different shape (e.g., dome, button, round, truss, mushroom, countersunk, oval, raised, bugle, cheese, fillister, flanged, or other cage head shape). In some examples, the opening in head 102 may have a receiving apparatus for a torque applying tool, such as driver. The driver may be flat head, Phillip's head, square head, hexagonal, head or any similar shape suitable to receive a tool and apply torque therefrom. In one example, the torque applying tool may be a driver having a TORX® or TORX®-like shape (i.e., six-point or six-lobed shape) configured to receive the tip of a TORX® or TORX®-like screwdriver (e.g., driver 902). For example, cage 100 may include head grooves 118a-118f which may start at head 102 and extend linearly into the cannula of cage 100 to receive complementary lobes on the end of a screwdriver. For a TORX® or TORX®-like opening there may be six (6) total head grooves, including, for example, head grooves 118a-118f, to receive the complementary lobes on the tip of a TORX® or TORX®-like driver. The opening in head 102 may be contiguous with, and form a top end of, cage 100's cannula. For example, the opening may provide access to the cannula, for example, to pack material into the cage. The opening may also include a chamfer 119 providing a lead-in for a tool into the head grooves.

As described herein, the therapeutic materials may include osteogenic compounds (e.g., bone morphogenetic protein, or other osteogenic compounds that may ossify tissue), osteoconductive materials (e.g., demineralized bone, hydroxyapatite, or other material that promotes bone growth), antibiotics, steroids, contrast materials, or other materials that may be beneficial to fusing the joint, treating inflammation or other conditions in the joint, or enabling the visualization of the area within and adjacent to the cage. For example, an osteogenic compound, such as bone morphogenetic protein or other compounds, may be packed into cage 100's cannula such that when cage 100 is inserted into a joint or traverses through a joint (e.g., a sacroiliac joint), the osteogenic compound, for example through fenestrations (e.g., fenestrations 107a-107h, 108a-108h, 109a-109h, and/or 110a-110h), may come into contact with tissue in the joint adjacent to or surrounding cage 100, and ossify the tissue to fuse the joint across and through the cage. In some examples, the osteogenic compound may enter the joint and may fill the joint, partially or entirely. In other examples, an osteoconductive material, such as demineralized bone or hydroxyapatite or other materials may be packed into cage 100's cannula. When cage 100 is inserted into a joint (e.g., the joint between ilium I and sacrum S), the osteoconductive material may come into contact with tissue in the joint adjacent to or surrounding cage 100, for example through fenestrations (e.g., fenestrations 107a-107h, 108a-108h, 109a-109h, and/or 110a-110h), and promote bone growth into the cage and the joint to fuse the joint across and through the cage. In still other examples, a substance for treating sacroiliitis, such as steroids or antibiotics or other substances, may be packed into cage 100's cannula such that when cage 100 is inserted into the joint, the substance may come into contact with tissue in the joint adjacent to or surrounding cage 100, for example through fenestrations (e.g., fenestrations 107a-107h, 108a-108h, 109a-109h, and/ or 110a-110h), and treat the inflamed joint tissue. In yet other examples, a contrast material may be packed into cage 100's cannula such that, when cage 100 is inserted into the joint, the contrast material within cage 100, and in some examples absorbed by tissue adjacent to or surrounding cage 100, may be viewed using visualization techniques (e.g., x-ray, fluoroscope, ultrasound, or other visualization technique). In still other examples, different materials may be packed into cage 100 for different purposes. In yet other examples, the above-described materials may also come into contact with tissue adjacent to, or surrounding, cage 100 through an opening at tip 104. As described herein, cage 100 may be packed with material prior to being inserted into the joint, and may also be packed after insertion into the joint. Also as described herein, such materials may be packed into cage 100 using a packing plunger 1102 (see, e.g., FIG. 9).

In some examples, fenestrations (e.g., fenestrations 107a-107h, 108a-108h, 109a-109h, and/or 110a-110h) may provide therapeutic openings in cage 100's shaft to enable material packed inside cage 100 to come into contact with surrounding or adjacent tissue (e.g., bone, cartilage, or other tissue in the joint) when cage 100 is implanted. Additionally or alternatively, in various examples, the fenestrations (e.g., fenestrations 107a-107h, 108a-108h, 109a-109h, and/or 110a-110h) may be shaped to provide additional cutting edges or edges suitable to clean threads formed by the tip 120. In various examples, fenestrations (e.g., fenestrations 107a-107h, 108a-108h, 109a-109h, and/or 110a-110h) are substantially circular. In other examples, the fenestrations (e.g., fenestrations 107a-107h, 108a-108h, 109a-109h, and/or 110a-110h) are oblong (e.g., substantially oval, substantially elliptical, or other suitable shapes). In other examples, fenestrations (e.g., fenestrations 107a-107h, 108a-108h, 109a-109h, and/or 110a-110h) are shaped differently (e.g., rectangular, rounded rectangular, squared, triangular, or other suitable shapes). In accordance with various embodiments and discussed herein As illustrated in FIGS. 6A and 6C, driver assembly 900 includes driver 902, mating tip 904, driver handle 906, tissue protector 404, handle 412, and tissue protector head 414. In some examples, driver 902 may be configured to drive a cage (e.g., cages 100) into a bone and/or joint. In some examples, driver 902 may have a shaft configured to fit or slide within tissue protector 404. In some examples, mating tip 904 may be shaped to engage (i.e., fit) a head of a cage (e.g., head 102). For example, driver 902 may be a TORX® driver and mating tip 904 may be shaped to fit a TORX® head cage (e.g., with a six-point or six-lobed shape). In other examples, mating tip 904 may be shaped differently to engage suitable types of cages (e.g., PHILLIPS™ (i.e., having a cruciform or cross shape with four lobes), slot, flat, Robertson, hex, or other type of cages). In some examples, driver handle 906 may be used to turn driver 902, and consequently turn a cage engaged by mating tip 904. In some examples, driver 902 may be a manual driver. In other examples, driver 902 may be powered (i.e., electrically). In some examples, driver 902 also may be ratcheting or torque-limited. In some examples, driver handle 906 may be formed separately from driver 902's shaft and driver tip 904. In some examples, handle 906 may be configured to be removably coupled with various types of drivers (e.g., TORX®, PHILLIPS™, slot, flat, Robertson, hex, or other types of cage drivers). In other examples, driver 902 and driver handle 906 may be formed differently, and are not limited to the examples shown and described. The cage 100 includes a cannula that slides over the guide wire 418 and into tissue protector sleeve 404. The driver 902 forces the cage 100 down sleeve 404 until contact is made with the bone. Then a torque is applied to cage 100 by the handle 906 causing the cage to twist into the bone.

Figure 7A:
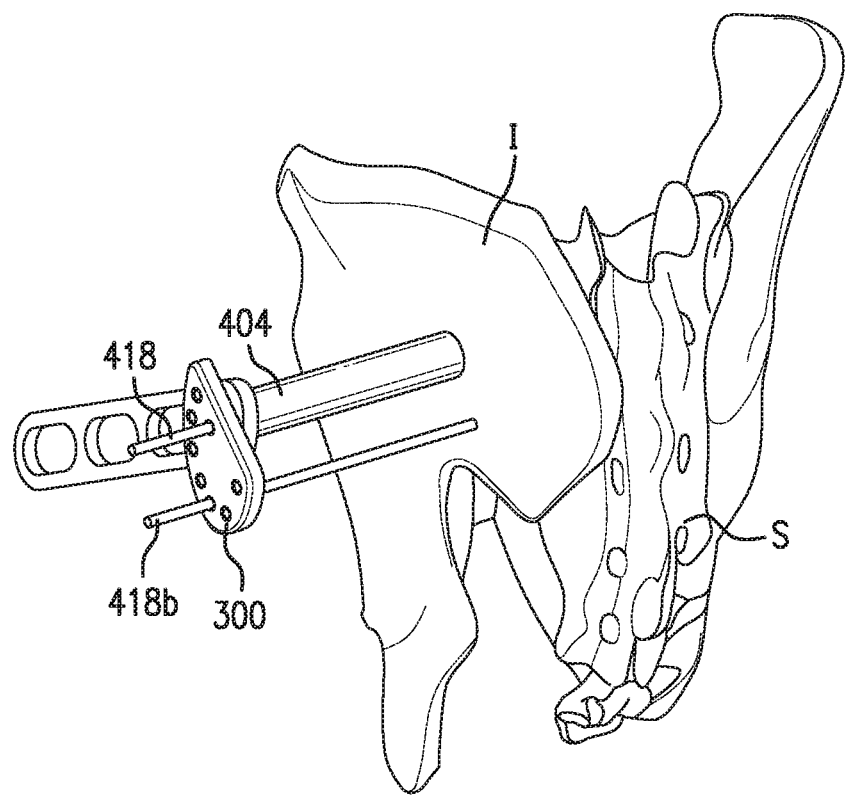
FIG. 7A is a perspective view of a parallel guide according to one embodiment being used to set a guide at a new location in a sacroiliac joint in the procedure of FIG. 3.

FIG. 7A is a perspective view of a parallel guide 300 according to one embodiment being used to set another guide at a new location in a sacroiliac joint in the procedure of FIG. 3. This embodiment of the parallel guide 300 corresponds to the parallel guide illustrated in FIG. 8A and discussed in more detail below.

Figure 8B:
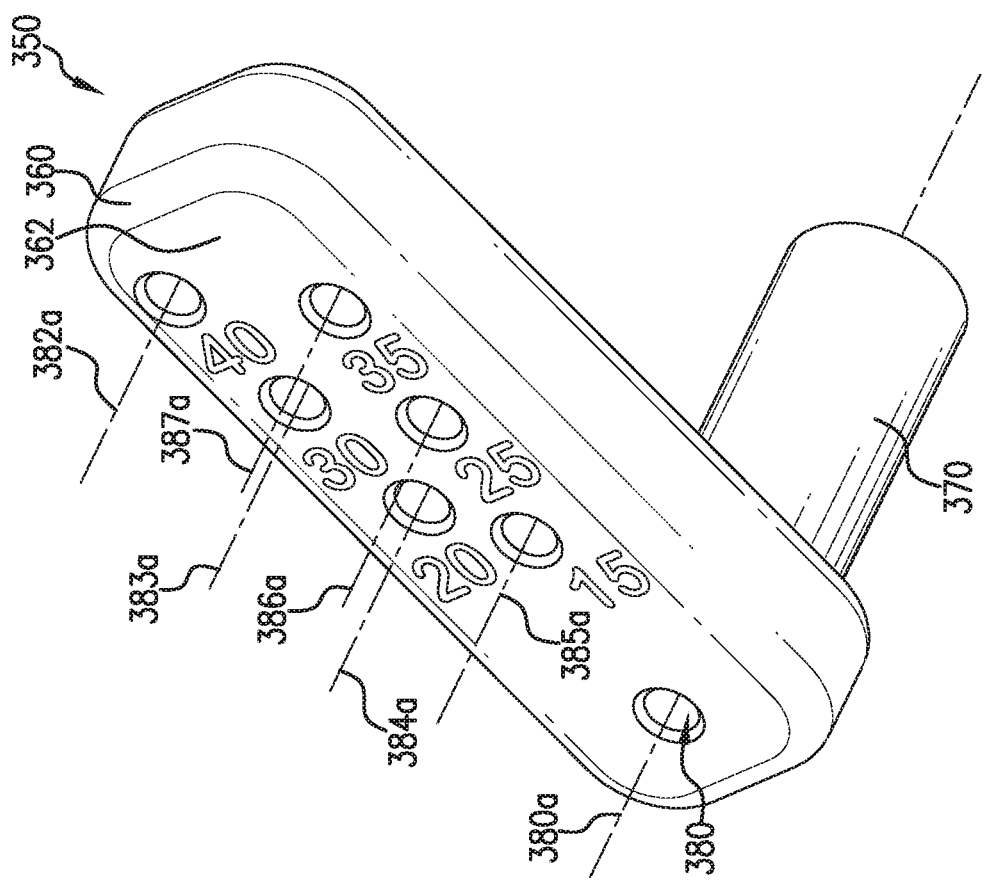
FIGS. 8A and 8B are a perspective views of a parallel guides for joint fusion according to various embodiments.
Figure 8A:
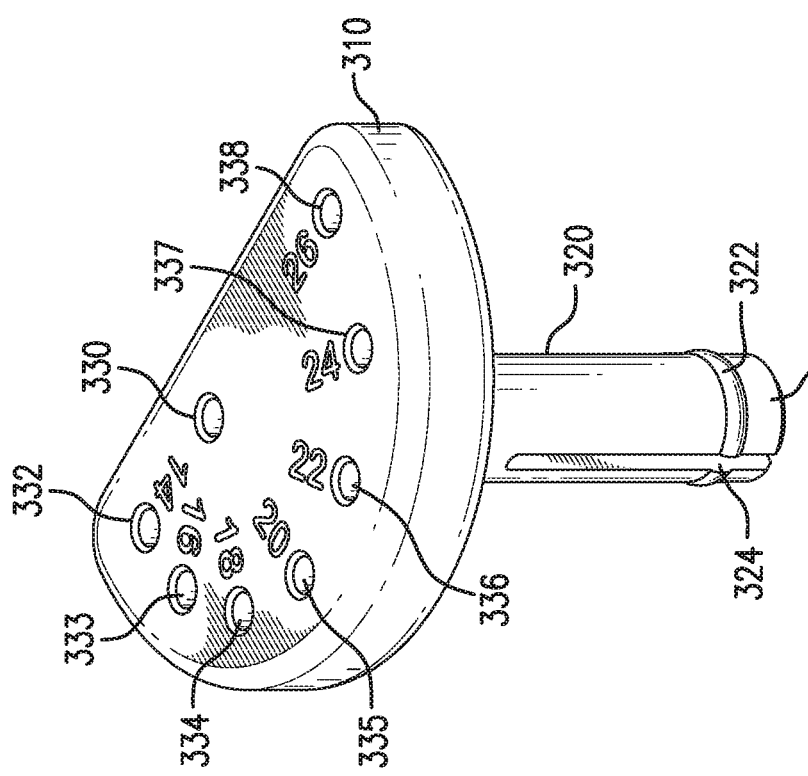

FIG. 8A illustrates a perspective view of a parallel guide 300 for joint fusion according to one embodiment. Here, the parallel guide 300 includes a parallel spacer body 310 and an external positioning protrusion 320. In accordance with various embodiments, the parallel spacer body 310 includes a plurality of apertures (e.g., apertures 330 or 332-338) suitable to receive one or more guides (e.g., guide pins 418a or 418b shown in FIGS. 3 and 7A). In accordance with various embodiments, the external positioning protrusion 320 extends from the parallel spacer body 310 and is suitable to engage with a tissue protector 400. In some examples, parallel guide 300 may be configured to place another or a next guide at a distance from a previously placed implant (i.e., a previously implanted screw or cage).

In accordance with various embodiments, the parallel guide 300 includes one or more subsequent guide apertures (e.g., apertures 332-338). Each of the plurality of subsequent guide apertures (e.g., apertures 332-338) are fixedly located relative to the primary guide aperture (e.g., aperture 330) thereby defining a set distance between each of the subsequent guide apertures (e.g., apertures 332-338) and the primary guide aperture (e.g., aperture 330). The subsequent guide apertures (e.g., apertures 332-338) may be integrally formed with parallel spacer body 310 along with the primary guide aperture (e.g., aperture 330) such that each distance (e.g., distance 342-348) is constant. In accordance with various embodiments, each of the subsequent guide apertures (e.g., apertures 332-338) extends through the parallel spacer body 310.

In some examples, parallel spacer body 300 may comprise spacer markings with numerical labels for measuring out the spacing between the primary guide 418 and the subsequently placed guide 418b. Any subsequently placed guide 418b is placed in the aperture corresponding to the spacer marking. The number corresponding to that marking may indicate the space (i.e., distance, for example, in millimeters) between a previously placed guide 418, and the guide 418b to be placed in subsequent guide aperture (e.g., aperture 332-338). This, in turn, may determine the spacing between an implant (e.g., cage or bone screw) and a next implant (e.g., cage or bone screw). By utilizing discrete apertures, as opposed to a continuously adjustable mechanism for locating the subsequent guide relative to the primary guide, consistent control over the surgical procedure can be obtained.

In accordance with one embodiment, the pattern of discrete locations for the aperture (e.g., aperture 332-338) can form an arc. The primary aperture (e.g., aperture 330) can be concentric within the arc. In one embodiment, the concentric location is selected such that there is a different distance between the primary aperture (e.g., aperture 330) and each of the other apertures (e.g., aperture 332-338) extending through the guide body 310. This results in a variety of different discrete distances that are usable in the surgical procedure for placing one guide (e.g., pin 418b) in a parallel configuration relative to another guide (e.g., pin 418). In one example, the distances between the primary aperture (e.g., aperture 330) and each of the other apertures (e.g., aperture 332-338) increases as the arc progresses from one side to the other.

In accordance with various embodiments, the external positioning protrusion 320 is suitably connected to the parallel spacer body 310 so as to constrain and/or position the tissue protector 400 relative to the parallel spacer body 310. For example, the external positioning protrusion 320 may be integrally formed with parallel spacer body 310. In one embodiment, the external protrusion may have an outer diameter suitable to be received into the tissue protector 400. In another embodiment, the external protrusion may have an inner diameter (e.g. along the aperture 330 which could be stepped in diameters to accommodate both the guide and the tissue protector) suitable to receive the tissue protector 400. In various embodiments, the external positioning protrusion 320 may function as the primary alignment member by engaging another alignment entity such as a drill guide or tissue protector. This allows the second guide 418b to be set parallel relative to the other alignment entity.

In some examples, external positioning protrusion 320 may be sized (i.e., have an outer diameter configured) to fit within the cannula of a drill guide, and also may have its own hollow shaft (i.e., an external positioning protrusion cannula) configured to fit around or over a guide. FIG. 7A illustrates a view of an exemplary parallel guide 300 for placement of another guide as placed on a drill guide: the parallel spacer body 310, external positioning protrusion 320, primary guide aperture 330, subsequent guide aperture 332, tissue protector 404, handle 412, and guide 418b. As shown, external positioning protrusion 320 may fit into tissue protector 404. In some embodiments, part of parallel spacer body may rest against tissue protector. In various embodiments, guide 418 may be inserted into the joint (e.g., by threading, hammer, pressing or similar method). For example, a press may press the guide into the bone approximately 1 mm-4 mm. A depth gauge may be used to measure the depth of the guide 418 into the joint. In some embodiments, the tissue protector 404 may be slid over the depth gauge 602 to locate the tissue protector 404, or in other embodiments, the tissue protector 404 may be located first and then the guide (e.g. pin 418) and depth gauge 602 are inserted into the tissue protector 404. The external positioning protrusion 320 may fit over guide 418 via aperture 330. In some examples, parallel guide 300 is placed on tissue protector 404. A next guide 418b, as shown in FIG. 7A, may be inserted through any one of the subsequent guide apertures (e.g., any one of apertures 332-338) until the end of the next guide 418b rests against a bone (i.e., an ilium). While in place in subsequent guide aperture (e.g., any one of apertures 332-338), the next guide 418b may be advanced into the bone and through a joint to a desired depth (e.g., using a mallet or other suitable method).

In some examples, parallel spacer body 300 may comprise spacer markings (e.g., markings 332e-338g) with numerical labels for measuring out the spacing between the primary guide 418 and the subsequently placed guide 418b. Any subsequently placed guide 418b is placed in the aperture corresponding to the spacer marking. The number corresponding to that marking may indicate the space (i.e., distance, for example, in millimeters) between a previously placed guide 418, and the guide 418b to be placed in subsequent guide aperture (e.g., aperture 332-338). This, in turn, may determine the spacing between an implant (e.g., cage or bone screw) and a next implant (e.g., cage or bone screw).

Figure 7B:
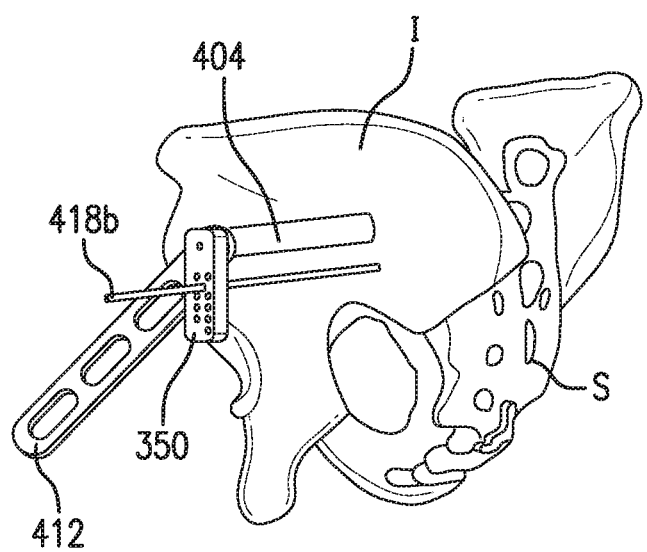
FIG. 7B is a perspective view of a parallel guide according to another embodiment being used to set a guide at a new location in a sacroiliac joint in the procedure of FIG. 3.

FIG. 7B is a perspective view of a parallel guide according to another embodiment being used to set a guide at a new location in a sacroiliac joint in the procedure of FIG. 3. This embodiment of the parallel guide 350 corresponds to the parallel guide illustrated in FIG. 8B and discussed in more detail above.

FIG. 8B is a perspective view of a parallel guide for joint fusion according to one embodiment. Here, the parallel guide 350 includes a parallel spacer body 360 and an external positioning protrusion 370. In accordance with various embodiments, the parallel spacer body 310 includes a plurality of apertures (e.g., apertures 380 or 382-337) suitable to receive one or more guides (e.g., guides 418a or 418b shown in FIGS. 3 and 7B). In accordance with various embodiments, the external positioning protrusion 370 extends from the parallel spacer body 360 and is suitable to engage with a tissue protector 400. In some examples, parallel guide 350 may be configured to place another or a next guide at a distance from a previously placed implant (i.e., a previously implanted screw or cage). Like-numbered and named elements in this view may describe the same or substantially similar elements as in previous or subsequent views.

In accordance with various embodiments, the parallel spacer body 360 includes a proximal surface 362 and a distal surface 364. While shown as opposing flat parallel surfaces, it is appreciated that these surfaces can have other suitable profiles, such as concave, convex and irregular surfaces. In accordance with various embodiments, the parallel spacer body 360 has a sufficient thickness to hold a guide in a substantially constant angular position relative to the parallel guide 350. The parallel spacer body 360 can be any suitable shape to position each of the various apertures therethrough. In one example, the proximal surface 362 is an elongated rectangle defining the overall shape of the parallel spacer body down to the distal surface 364 which is also a semi-circle. Other shapes, such as circles, polygons (triangles, other rectangles, etc.), or less geometrical shapes may be suitable as well.

In accordance with various embodiments, the primary guide aperture (e.g., aperture 380) extends through the parallel spacer body 360. The primary guide aperture (e.g., aperture 380) includes an axis 380a that defines the orientation of the guide (e.g., guide 418) relative to the parallel guide 350 as the guide passes through the aperture. The primary guide aperture (e.g., aperture 380) includes an opening 380b on the proximal end of the parallel guide 350. In one example, the opening 380b extends into the parallel spacer body 360 from the proximal surface 362. In other examples, the opening 380b may extend into the parallel spacer body 360 from any suitable surface on the proximal end of the parallel guide 350, such as a protrusion on the proximal end or like feature.

In accordance with various embodiments, the parallel guide 350 includes one or more subsequent guide apertures (e.g., apertures 382-387). Each of the plurality of subsequent guide apertures (e.g., apertures 382-387) are fixedly located relative to the primary guide aperture (e.g., aperture 380) thereby defining a set distance between each of the subsequent guide apertures (e.g., apertures 382-387) and the primary guide aperture (e.g., aperture 380). The subsequent guide apertures (e.g., apertures 382-387) may be integrally formed with parallel spacer body 360 along with the primary guide aperture (e.g., aperture 380) such that each distance (e.g., distance 392-398) is constant.

In accordance with one embodiment, the pattern of discrete locations for the aperture (e.g., aperture 382-387) can extend from aperture 380 in separate linear formation. As indicated above, each of the apertures (e.g., apertures 382-387) can form a separate line with aperture 380 being the first point and apertures 382-387 being separate distinct separate points forming separate lines with aperture 380. However to form a smaller body, 360 each of the apertures (e.g., aperture 382-387) can group together into separate lines. For example half of the apertures can be in one line and half of the apertures can be in the other. The apertures can alternate between lines with increasing distance from aperture 380. For example, apertures (e.g., apertures 382-387) can increase in distances from aperture 380 in according to a progression: aperture 385, then aperture 384, then aperture 386, then aperture 383, then aperture 387, then aperture 382. But each of apertures 385, 386, and 387 can fall along one line 397 from aperture 380 and each of apertures 384, 383, and 382 can fall along another line 398 from aperture 380. This arrangement allows smaller steps in distances between apertures, without the aperture contacting each other. In one example, each of the apertures in a line (e.g. line 398) are separated from each by about the distance of one aperture diameter. This results in that ability to step the apertures alternatively between the lines in steps equal to the aperture diameter. In another example, each of the apertures in a line can be separated from one another by a distance of less than the aperture diameter. This results in that ability to step the apertures alternatively between the lines in steps less than the aperture diameter. In another example, each of the apertures in a line can be separated from one another by a distance of more than the aperture diameter. Additionally, more lines of apertures can be incorporated.

Examples of the parallel spacer, such as parallel spacer 300 and 350 are further disclosed in co-pending application entitled "Parallel Guides for Surgical implants" having application Ser. No. 15/799,419 filed herewith on the same date, which is incorporated herein by reference in its entirety.

Figure 9:
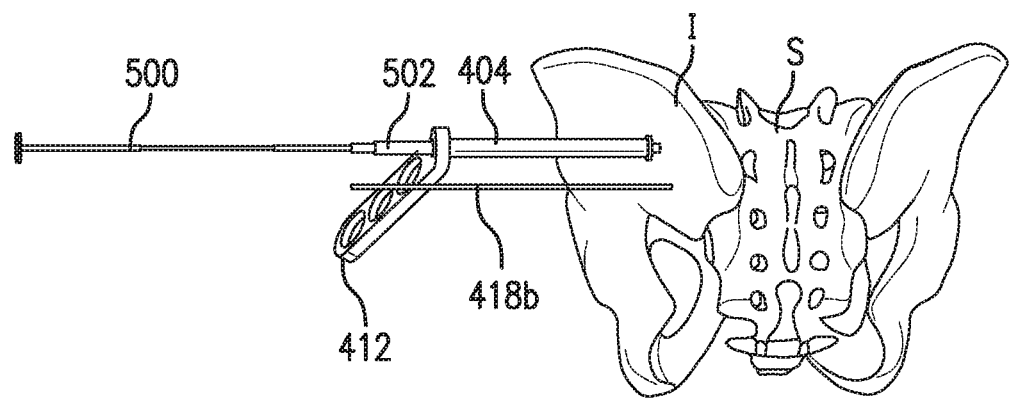
FIG. 9 illustrates a packing plunger assembly according to one embodiment placed in a tissue protector assembly for packing a cage for joint fusion in the procedure of FIG. 3.

FIG. 7A illustrates a side view of the parallel guide 300 for placement of another guide 418b. FIG. 9 illustrates a second guide 418b placed parallel to the first setup. This is accomplished by running the additional guide 418b through the spacer block. In some examples, guide 418 may still be in place within tissue protector 400. Once the parallel guide 300 is placed on tissue protector 400, a next guide 418b is inserted through the parallel spacer reaching down to engage the bone (e.g., an ilium).

FIG. 9 illustrates a perspective view of an exemplary packing plunger 500 placed in a dispensing tube 502. In some examples, dispensing tube 502 and plunger 500 work together to dispense therapeutic material into the cage located in the bone (e.g., ilium and/or sacrum). The plunger and the dispensing tube dispense various therapeutic materials (e.g., liquids, gases, gels, or other materials. As described herein, such therapeutic materials include osteogenic compounds (e.g., bone morphogenetic protein, or other osteogenic compounds that may ossify tissue in the joint), osteoconductive materials (e.g., demineralized bone, hydroxyapatite, or other material that promotes bone growth), antibiotics, steroids, contrast materials, or other materials that may beneficial to fusing the joint, treating inflammation or other conditions in the joint, or enabling the visualization of the area within and adjacent to the cage. In some examples, plunger 500 may be depressed to dispense material from dispensing tube 502, for example, into a cannulated cage (e.g., cages 100), which may in turn deliver said material into a joint, as described above, through the fenestrations discussed above.

In accordance with the various embodiments, a particular method of using a tissue protector may include inserting a first guide pin through an incision to the bone and sinking the guide pin into the bone. A tissue dilator is advanced over the first guide pin until the tissue dilator reaches the bone. A tissue protector is advanced over the tissue dilator until the tissue protector reaches the bone without significantly penetrating the bone with the tissue protector. The tissue dilator is removed from inside the tissue protector leaving the first guide pin in situ. A press or drill bit is aligned along the guide pin and through the tissue protector. The press or drill bit bores into and/or threads into the bone. In some embodiments, the press/drill bit presses a drill guide into the bone tissue. In other embodiments, a drill bit bores into the bone and the tissue protector floats outside of the bone protecting the surrounding tissue from the drill and implants. The drill bit/press is removed from the pin. An implant is aligned over the first guide pin. The implant is driven into the bone. A primary aperture of a parallel guide is aligned over the first guide pin. A second guide pin is located relative to the first guide pin by sliding the second guide pin through a secondary aperture in the parallel guide, thereby locating the second guide pin parallel to the guide pin and independent of the orientation of the tissue protector. The second guide pin is inserted through an incision to the bone and sinks the guide pin into the bone. The guide pin is an insulated pin configured to be electrically stimulated which causes contraction of the nearby muscle tissue. An electrical stimulator lead is attached to the guide pin prior to advancing the guide pin. Electrical stimulation is provided through the guide pin while inserting the guide pin into the bone. The guide pin is driven across the sacroiliac joint space. The guide pin is driven to about 1 cm away from the anterior sacral wall. A drill bit is advanced over the guide pin and drill opening into the bone. In various examples, the implant is a bone cage. The length of the implant is coordinated with markings on the dilator as indicated by the extent to which the guide pin extends up the length of the dilator. The parallel guide has discrete primary and secondary apertures that are at a fixed distance relative to one another. After insertion of the second guide pin, the process is for implantation of a second implant. The first guide pin is removed after locating the second guide pin and then packing the implant with therapeutic material.

Although the foregoing examples have been described in some detail for purposes of clarity of understanding, the invention is not limited to the details provided. There are many alternative ways of implementing the invention.

What is claimed is:
1. A surgical press for setting a surgical device into bone, the surgical press system comprising:
   an elongated shaft having a distal portion and a proximal portion, the shaft being configured for insertion into a guide;
   threads extending along an axial portion of the distal portion of the shaft, wherein the threads are configured to pull the shaft into bone as the shaft rotates;
   a press element associated with the proximal portion of the shaft such that as the shaft is rotated, the threads pull the shaft into the bone causing the press element to press the surgical device into the bone;
   a collection region located in the distal portion of the shaft and configured to receive bone material removed from the bone due to advancement of the shaft; and a locating element configured to position the surgical device in a predetermined orientation with respect to the shaft as the press element presses the surgical device into the bone.

2. The press system of claim 1, wherein the threads are configured to tap a thread path into the bone as the threads pull the shaft into the bone.

3. The press system of claim 1, further comprising cutting flutes extending along the distal portion of the cannulated shaft.

4. The press system of claim 3, wherein the threads are proximal of a proximal termination of the cutting flutes and are suitable to tap a path cut by the cutting flutes.

5. The press system of claim 4, wherein the locating element includes an expanded body portion extending from the shaft proximal of the threads and the cutting flutes and distal of the press element, wherein the expanded body portion is sized to an interior diameter of the surgical device such that the shaft and the surgical device maintain alignment together.

6. The press system of claim 3, wherein the shaft is cannulated and configured to receive and be guided by a guide pin.

7. The press system of claim 3, wherein the press element is integral to and extends radially from the shaft.

8. The press system of claim 7, wherein the press element protrudes from the shaft and is larger in diameter than portions of the shaft distal of the press element.

9. The press system of claim 7, further comprising the surgical device which includes a sleeve that is suitable to separate the shaft from surrounding tissue while the cutting flutes cut into the bone and the threads pull the sleeve into the bone.

10. The press system of claim 9, wherein the press element forms a protrusion extending from the shaft that is configured to contact a distal end of the surgical device exerting a force thereon as the threads pull the sleeve into the bone.

11. The press system of claim 10, wherein the protrusion is annular and configured to contact evenly on a proximal end of the surgical device.

12. The press system of claim 11, wherein the surgical device is a guide that is configured to establish an angular orientation for the system once the guide is pressed into and set in the bone.

13. The press system of claim 1, wherein the collection region is configured to accumulate or distribute the bone material to limit interference with the advancement of the shaft in the bone.

14. A drill bit configured to drill a pilot hole in a bone tissue, the pilot hole configured to receive an implant, the drill bit comprising:
an elongated cannulated shaft having a distal end and a proximal end;
cutting flutes extending along a distal portion of the cannulated shaft, wherein the cutting flutes are configured to form the pilot hole in the bone tissue that receives an implant; and
threads extending along the distal portion of the cannulated shaft and proximal of the cutting flutes, wherein the threads are configured to tap the pilot hole and pull the cannulated shaft into bone tissue as the cannulated shaft rotates; and a press element associated with a proximal portion of the shaft such that as the shaft is rotated, the threads pull the shaft into the bone tissue causing the press element to press a surgical device into the bone tissue.

15. A surgical press system comprising:
the drill bit of claim 14, wherein:
the shaft has a first diameter, and
the drill bit includes a locating element formed of an annular protrusion extending outwardly from the shaft and having a locating element diameter greater than the first diameter of the shaft;
a tissue protector defining an interior channel that has an inside diameter that is sufficiently larger than the locating element diameter to receive the locating element such that the drill bit can slide and rotate within the tissue protector; and
wherein the press element has a larger diameter than the inside diameter such that the press element is configured to limit the shaft from advancing farther into the tissue protector.

16. The surgical press system of claim 15, wherein the press element is annular and configured to contact evenly on the proximal end of the surgical device.

17. The drill bit of claim 14, further comprising a locating element configured to position the surgical device in a predetermined orientation with respect to the shaft as the press element presses the surgical device into the bone tissue.

18. The drill bit of claim 14, wherein the cannulated shaft is sized to slide over a guide pin.

19. The drill bit of claim 14, wherein the shaft includes a shank on the proximal end, suitable to engage a handle or drill.

20. The drill bit of claim 14, further comprising a collection region located distal of the threads, the collection region forming a volume that is configured to accumulate or distribute material removed by the threads.

21. A drill bit configured to drill a pilot hole in a bone tissue, the pilot hole configured to receive an implant, the drill bit comprising:
an elongated cannulated shaft having a distal end and a proximal end;
cutting flutes extending along a distal portion of the cannulated shaft, wherein the cutting flutes are configured to form the pilot hole in the bone tissue that receives an implant;
threads extending along the distal portion of the cannulated shaft and proximal of the cutting flutes, wherein the threads are configured to tap the pilot hole and pull the cannulated shaft into bone tissue as the cannulated shaft rotates; and
a collection region located distal of the threads, the collection region forming a volume that is configured to accumulate or distribute material removed by the threads.

22. The drill bit of claim 21, wherein:
the cannulated shaft is sized to slide over a guide pin, and
the shaft includes a shank on the proximal end, suitable to engage a handle or drill.

* * * * *